US007060112B2

(12) United States Patent
Lang et al.

(10) Patent No.: US 7,060,112 B2
(45) Date of Patent: Jun. 13, 2006

(54) COMPOSITION FOR THE OXIDATION DYEING OF KERATINOUS FIBERS CONTAINING A LACCASE AND DYEING METHOD USING THIS COMPOSITION

(75) Inventors: Gérard Lang, Saint Prix (FR); Jean Cotteret, Vermeuil sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/826,333

(22) Filed: Apr. 19, 2004

(65) Prior Publication Data

US 2004/0255401 A1    Dec. 23, 2004

Related U.S. Application Data

(63) Continuation of application No. 09/600,133, filed as application No. PCT/FR98/02834 on Dec. 22, 1998, now abandoned.

(30) Foreign Application Priority Data

Jan. 13, 1998  (FR) .................................. 98 00256
Jul. 22, 1999  (FR) .................................. 99 36042

(51) Int. Cl.
*A61K 7/13* (2006.01)
(52) U.S. Cl. ...................... 8/405; 8/401; 8/408; 8/409; 8/411; 8/412; 8/421
(58) Field of Classification Search ................ 8/405, 8/408, 409, 411, 412, 401, 421
See application file for complete search history.

(56) References Cited

U.S. PATENT DOCUMENTS

| 3,251,742 | A | 5/1966 | Soloway .................... 167/88 |
| 4,003,699 | A | 1/1977 | Rose et al. .................. 21/0.2 |
| 4,823,985 | A | 4/1989 | Grollier et al. ............... 222/1 |
| 5,061,289 | A | 10/1991 | Clausen et al. ............... 8/405 |
| 5,380,340 | A | 1/1995 | Neunhoeffer et al. .......... 8/409 |
| 5,710,311 | A | 1/1998 | Junino et al. ............... 558/414 |
| 5,766,576 | A | 6/1998 | Lowe et al. .................. 424/62 |
| 5,849,041 | A | 12/1998 | Kunz et al. .................. 8/408 |
| 6,090,160 | A | * 7/2000 | Junino et al. ................ 8/409 |
| 6,129,770 | A | 10/2000 | Deutz et al. .................. 8/406 |
| 6,383,231 | B1 | 5/2002 | Lang et al. ................... 8/405 |
| 6,471,730 | B1 | 10/2002 | Lang et al. ................... 8/405 |
| 6,537,328 | B1 | 3/2003 | Lang et al. ................... 8/405 |
| 6,551,359 | B1 | 4/2003 | Lang et al. ................... 8/405 |
| 6,576,024 | B1 | 6/2003 | Lang et al. ................... 8/405 |
| 6,599,329 | B1 | 7/2003 | Lang et al. ................... 8/405 |
| 6,626,962 | B1 | 9/2003 | Lang et al. ................... 8/405 |
| 6,893,470 | B1 | 5/2005 | Lang et al. ................... 8/401 |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| DE | 196 47 494 | 4/1998 |
| EP | 0 504 005 | 9/1992 |
| EP | 0 795 313 | 9/1997 |
| FR | 2 112 549 | 6/1972 |
| FR | 2 586 913 | 3/1987 |
| FR | 2 694 018 | 1/1994 |
| FR | 2 733 749 | 11/1996 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/15765 | 5/1996 |
| WO | WO 97/19998 | * 6/1997 |
| WO | WO 97/19999 | 6/1997 |

OTHER PUBLICATIONS

English Language Derwent Abstract of EP 0 504 005.
English Language Derwent Abstract of FR 2 112 549.
English Language Derwent Abstract of FR 2 694 018.
English Language Derwent Abstract of FR 2 733 749.
English Language Derwent Abstract of JP 2-19576.
English Language Derwent Abstract of JP 5-163124.
English Language Derwent Abstact of DE 196 47 494.

* cited by examiner

*Primary Examiner*—Eise Elhilo
(74) *Attorney, Agent, or Firm*—Finnegan Henderson Farabow Garrett & Dunner, L.L.P.

(57) ABSTRACT

The invention relates to a composition for oxidation dyeing of keratinous fibers, and in particular human keratinous fibers, such as hair, comprising, in a medium appropriate for dyeing, at least one oxidation base, 2-amino-4-N-(β-hydroxyethyl)aminoanisole as coupler, and at least an enzyme of the laccase type, as well as the dyeing method using this composition.

36 Claims, No Drawings

COMPOSITION FOR THE OXIDATION DYEING OF KERATINOUS FIBERS CONTAINING A LACCASE AND DYEING METHOD USING THIS COMPOSITION

This application is continuation of a U.S. application Ser. No. 09/600,133, filed on Oct. 3, 2000 which is abandoned on May 5, 2004 and which is a 371 of PCT/FR98/02834 filed on Dec. 22, 1998.

The subject of the invention is a composition for the oxidation dyeing of keratinous fibres, and in particular of human keratinous fibres such as hair, comprising, in a medium appropriate for dyeing, at least one oxidation base, 2-amino-4-N-(β-hydroxy-ethyl)aminoanisole as coupler, and at least one enzyme of the laccase type, as well as the dyeing method using this composition.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, (oxidation bases), are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in Patent U.S. Pat. No. 3,251,742, Patent Applications FR-A-2,112,549, FR-A-2,694,018, EP-A-0,504,005, WO95/07988, WO95/33836, WO95/33837, WO96/00290, WO97/19998 and WO97/19999 to dye keratinous fibres with compositions comprising at least one oxidation dye, or at least one melanin precursor, in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre (unison), from the point of view of chromaticity (luminosity) and of the dyeing power.

Now, the applicant has now just discovered that it is possible to obtain novel dyes which are capable of giving intense and chromatic colours, without causing significant degradation of the keratinous fibres, which are not very selective and which are quite resistant to various attacks to which the fibres may be subjected, by combining at least one oxidation base, 2-amino-4-N-(β-hydroxyethyl)-aminoanisole as coupler, and at least one enzyme of the laccase type.

This discovery forms the basis of the present invention.

The first subject of the invention is therefore a ready-to-use composition for the oxidation dyeing of keratinous fibres, and in particular human keratinous fibres such as hair, characterized in that it comprises, in a medium appropriate for dyeing:

at least one oxidation base,
2-amino-4-N-(β-hydroxyethyl)aminoanisole and/or at least one of its addition salts with an acid as coupler,
at least one enzyme of the laccase type.

The ready-to-use dyeing composition in accordance with the invention gives intense colours which exhibit low selectivity and excellent properties of resistance both to atmospheric agents such as light and adverse weather conditions and to perspiration and various treatments to which the hair may be subjected (washing, permanent deformation).

The subject of the invention is also a method for the oxidation dyeing of keratinous fibres using this ready-to-use dyeing composition.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. The laccase(s) used in the ready-to-use dyeing composition in accordance with the invention can also be obtained by biotechnology.

Among the laccases of plant origin which can be used according to the invention, there may be mentioned the laccases produced by plants which perform chlorophyll synthesis such as those indicated in Patent Application FR-A-2,694,018.

There may be mentioned in particular the laccases present in the extracts of *Anacardiaceae* such as for example the extracts of *Magnifera indica, Schinus molle* or *Pleiogynium timoriense*, in the extracts of *Podocarpaceae, Rosmarinus* off., *Solanum tuberosum, Iris* sp., *Coffea* sp., *Daucus carrota, Vinca minor, Persea americana, Catharenthus roseus, Musa* sp., *Malus pumila, Gingko biloba, Monotropa hypopithys* (Indian pipe), *Aesculus* sp., *Acer pseudoplatanus, Prunus persica* and *Pistacia palaestina*.

Among the laccases of fungal origin, optionally obtained by biotechnology, which can be used according to the invention, there may be mentioned the laccase(s) derived from *Polyporus versicolor, Rhizoctonia practicola* and *Rhus vernicifera* as described for examples in Patent Applications FR-A-2,112,549 and EP-A-504005, the laccases described in Patent Applications WO95/07988, WO95/33836, WO95/33837, WO96/00290, WO97/19998 and WO97/19999, whose content is an integral part of the present description, such as for example the laccase(s) derived from *Scytalidium, Polyporus pinsitus, Myceliophtora thermophila, Rhizoctonia solani, Pyricularia orizae,* and variants thereof. There may also be mentioned the laccase(s) derived from *Trametes versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lac-*

*tarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens,* and variants thereof.

The laccases of fungal origin optionally obtained by biotechnology will be preferably chosen.

The enzymatic activity of the laccases used in accordance with the invention and which have syringaldazine among their substrates can be defined from the oxidation of syringaldazine under aerobic conditions. The Lacu unit corresponds to the quantity of enzyme catalysing the conversion of 1 mmol of syringaldazine per minute at a pH of 5.5 and at a temperature of 30° C. The unit U corresponds to the quantity of enzyme producing a delta absorbance of 0.001 per minute, at a wavelength of 530 nm, using syringaldazine as substrate, at 30° C. and at a pH of 6.5. The enzymatic activity of the laccases of the invention can also be defined from the oxidation of para-phenylenediamine. The lacu unit corresponds to the quantity of enzyme producing a delta absorbance of 0.001 per minute, at a wavelength of 496.5 nm, using para-phenylenediamine as substrate (64 mM), at 30° C. and at a pH of 5.

According to the invention, it is preferable to determine the enzymatic activity in lacu units.

The quantity of laccase(s) present in the ready-to-use dyeing composition in accordance with the invention will vary according to the nature of the laccase(s) used. Preferably, the quantity of laccase(s) is between 0.5 and 200 Lacu approximately that is to say between 10,000 and $4 \times 10^6$ U units approximately or that is to say between 20 and $2 \times 10^6$ lacu units, per 100 g of dyeing composition.

The nature of the oxidation base(s) used in the ready-to-use dyeing composition is not critical. They may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (I) and their addition salts with an acid:

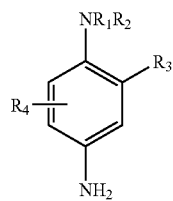

(I)

in which:

$R_1$ represents a hydrogen atom, a $C_1$–$C_4$ alkyl radical, a monohydroxy($C_1$–$C_4$ alkyl) radical, a polyhydroxy-($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_2$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, $R_4$ represents a hydrogen or halogen atom or a $C_1$–$C_4$ alkyl radical.

Among the nitrogen-containing groups of formula (I) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylene-diamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

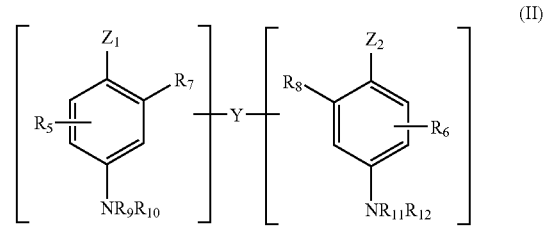

(II)

in which:
  $Z_1$ and $Z_2$, which are identical or different, represent a hydroxyl or —$NH_2$ radical which may be substituted with a $C_1$–$C_4$ alkyl radical or with a linking arm Y;
  the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or $C_1$–$C_6$ alkoxy radicals;
  $R_5$ and $R_6$ represent a hydrogen or halogen atom, a $C_1$–$C_4$ alkyl radical, a monohydroxy($C_1$–$C_4$ alkyl) radical, a polyhydroxy($C_2$–$C_4$ alkyl) radical, an amino($C_1$–$C_4$ alkyl) radical or a linking arm Y;
  $R_7$, $R_8$, $R_9$, $R_{10}$, $R_{11}$ and $R_{12}$, which are identical or different, represent a hydrogen atom, a linking arm Y or a $C_1$–$C_4$ alkyl radical;

it being understood that the compounds of formula (II) contain only one linking arm Y per molecule.

Among the nitrogen-containing groups of formula (II) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylene-diamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (III), and their addition salts with an acid:

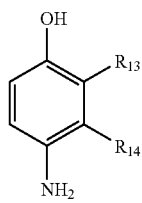

(III)

in which:
  $R_{13}$ represents a hydrogen or halogen atom, a $C_1$–$C_4$ alkyl, monohydroxy($C_1$–$C_4$ alkyl), ($C_1$–$C_4$) alkoxy($C_1$–$C_4$)-alkyl, amino($C_1$–$C_4$ alkyl) or hydroxy($C_1$–$C_4$)alkylamino-($C_1$–$C_4$ alkyl) radical,
  $R_{14}$ represents a hydrogen or halogen atom, a $C_1$–$C_4$ alkyl, monohydroxy($C_1$–$C_4$ alkyl), polyhydroxy($C_2$–$C_4$ alkyl), amino($C_1$–$C_4$ alkyl), cyano($C_1$–$C_4$ alkyl) or ($C_1$–$C_4$)alkoxy($C_1$–$C_4$)alkyl radical, it being understood that at least one of the radicals $R_{13}$ or $R_{14}$ represents a hydrogen atom.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl- 3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

Among the pyrazolopyrimidine derivatives, there may be mentioned more particularly the compounds described in Patent Application FR-A-2,750,048, among which there may be mentioned:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and their addition salts and their tautomeric forms, when a tautomeric equilibrium exists.

The oxidation base(s) preferably represent from 0.0005 to 12% by weight approximately of the total weight of the dyeing composition in accordance with the invention, and still more preferably from 0.005 to 6% by weight approximately of this weight.

The 2-amino-4-N-(β-hydroxyethyl)aminoanisole and/or the or its addition salts with an acid preferably represent from 0.0001 to 8% by weight approximately of the total weight of the dyeing composition, and still more preferably from 0.005 to 5% by weight approximately of this weight.

The dyeing composition in accordance with the invention may contain one or more other couplers different from 2-amino-4-N-(β-hydroxyethyl)aminoanisole and/or direct dyes in particular in order to modify the shades or to increase their shimmer.

Among the couplers which can additionally be present in the ready-to-use dyeing composition in accordance with the invention, there may be mentioned in particular meta-phenylenediamines, meta-aminophenols, meta-diphenols, and their addition salts with an acid.

When they are present these additional couplers preferably represent from 0.0001 to 10% by weight approximately of the total weight of the ready-to-use dyeing composition, and more preferably from 0.005 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The medium appropriate for dyeing (or carrier) of the ready-to-use dyeing composition in accordance with the invention generally consists of water or of a mixture of water and of at least one organic solvent in order to solubilize the compounds which might not be sufficiently soluble in water.

The pH of the ready-to-use composition in accordance with the invention is chosen such that the enzymatic activity of the laccase is sufficient. It is generally between 4 and 11 approximately, and preferably between 6 and 9 approximately. It may be adjusted to the desired value using acidifying or alkalinizing agents normally used in dyeing keratinous fibres.

The ready-to-use dyeing composition in accordance with the invention may also contain various adjuvants conventionally used in hair dyeing compositions, such as anionic, cationic, nonionic, amphoteric or zwitterionic surfactants or mixtures thereof, polymers, antioxidants, enzymes different from the laccases used in accordance with the invention, such as for examples peroxidases or oxidoreductases containing 2 electrons, penetrating agents, sequestering agents, perfumes, buffers, dispersing agents, thickening agents, film-forming agents, preservatives, opacifying agents or vitamins.

Of course, persons skilled in the art will be careful to choose this or these optional additional compounds such that the advantageous properties intrinsically attached to the ready-to-use dyeing composition in accordance with the invention are not, or substantially not, impaired by the addition(s) envisaged.

The ready-to-use dyeing composition in accordance with the invention can be provided in various forms, such as in the form of liquids, creams, gels, optionally pressurized, or in any other form appropriate for dyeing keratinous fibres, in particular human hair. In this case, the oxidation dyes and the enzyme(s) of laccase type are present in the same ready-to-use composition, and consequently the said composition should be free of gaseous oxygen, so as to avoid any premature oxidation of the oxidation dye(s).

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation base and 2-amino-4-N-(β-hydroxyethyl)aminoanisole and/or at least one of its addition salts with an acid, on the other hand, a composition (B) containing, in a medium appropriate for dyeing, at least one enzyme of the laccase type, and then in mixing them at the time of use before applying this mixture to the keratinous fibres.

Another subject of the invention is a multi-compartment device or dyeing (kit) or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The example which follows is intended to illustrate the invention without limiting the scope as a result.

DYEING EXAMPLE

The following dyeing composition was prepared:

| | |
|---|---|
| para-Phenylenediamine | 0.2 g |
| 2-Amino-4-N-(β-hydroxyethyl)aminoanisole dihydrochloride | 0.25 g |
| Laccase derived from Rhus vernicifera containing 180 units/mg sold by the company Sigma | 1.8 g |
| ($C_8$–$C_{10}$)Alkyl polyglucoside in aqueous solution containing 60% of active substance (AS) sold under the name ORAMIX | 8.0 g |

| | |
|---|---|
| CG110 ® by the company SEPPIC | |
| Ethanol | 20 g |
| pH agent qs | pH 6.5 |
| Demineralized water qs | 100 g |

The ready-to-use dyeing composition described above was applied to locks of natural grey hair which is 90% white for 40 minutes, at a temperature of 30° C. The hair was then rinsed, and then dried.

The hair was dyed in a blue grey shade.

In the dyeing composition described above, *Rhus vernicifera* laccase at 180 units/mg, sold by the company Sigma can be replaced by 1.0 g of *Pyricularia orizae* laccase at 100 units/mg sold by the company ICN.

What is claimed is:

1. A composition for the oxidation dyeing of keratinous fibers comprising:
   (a) at least one colorant chosen from oxidation bases and acid addition salts thereof;
   (b) at least one coupler chosen form 2-amino4-N-(β-hydroxyethyl)aminoanisole and acid addition salts of said coupler; and
   (c) at least one enzyme of the laccase type.

2. The composition according to claim 1, wherein said keratinous fibers are human keratinous fibers.

3. The composition according to claim 2, wherein said human keratinous fibers are hair.

4. The composition according to claim 1, wherein said at least one enzyme of the laccase type is chosen from laccases of plant origin, laccases of animal origin, laccases of fungal origin, and laccases of bacterial origin; and laccases obtained by biotechnology.

5. The composition according to claim 1, wherein said at least one enzyme of the laccase type is of plant origin and is chosen from the laccases extracted from plants chosen from *Anacardiaceae, Podocarpaceae, Rosmarinus* off., *Solanum tuberosum, Iris* sp., *Coffea* sp., *Daucus carrota, Vinca minor, Persea americana, Catharenthus roseus, Musa* sp., *Malus pumila, Gingko biloba, Monotropa hypopithys Aesculus* sp., *Acer pseudoplatanus, Prunus persica,* and *Pistacia palaestina*.

6. The composition according to claim 1, wherein said at least one enzyme of the laccase type is chosen from laccases of fungal origin and laccases obtained by biotechnology.

7. The composition according to claim 1, wherein said at least one enzyme of the laccase type is chosen from the laccases derived from fungi chosen from *Polyporus versicolor, Rhizoctonia praticola, Rhus vemicifera, Scytalidium, Polyporus pinsitus, Myceliophtora thermophila, Rhizoctonia solani, Pyricularia orizae, Tramates versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens,* and variants of all said fungi.

8. The composition according to claim 1, wherein said at least one enzyme of the laccase type is present in a quantity ranging from 0.5 to 200 Lacu units per 100 g of said composition.

9. The composition according to claim 1, wherein said oxidation bases are chosen from para-phenylenediamines, double bases, para-aminophenols, ortho-aminophenols, heterocyclic oxidation bases, and their acid addition salts.

10. The composition according to claim 9, wherein said para-phenylenediamines are chosen from compounds of the following formula (I) and their acid addition salts:

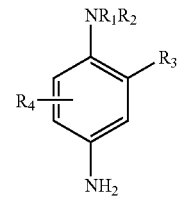

in which:

$R_1$ is chosen from hydrogen, $C_1$–$C_4$ alkyl groups, monohydroxy($C_1$–$C_4$ alkyl) groups, polyhydroxy-($C_2$–$C_4$ alkyl) groups, ($C_1$–$C_4$)alkoxy($C_1$–$C_4$)alkyl groups, $C_1$–$C_4$ alkyl groups substituted with a nitrogen-containing group, phenyl groups, and 4'-aminophenyl groups;

$R_2$ is chosen from hydrogen, $C_1$–$C_4$ alkyl groups, monohydroxy($C_1$–$C_4$ alkyl) groups, polyhydroxy-($C_2$–$C_4$ alkyl) groups, ($C_1$–$C_4$)alkoxy($C_1$–$C_4$)alkyl groups, and $C_1$–$C_4$ alkyl groups substituted with a nitrogen-containing group;

$R_3$ is chosen from hydrogen, halogens, $C_1$–$C_4$ alkyl groups, monohydroxy ($C_1$–$C_4$ alkyl) groups, hydroxy ($C_1$–$C_4$ alkoxy) groups, acetylamino($C_1$–$C_4$ alkoxy) groups, mesylamino($C_1$–$C_4$ alkoxy) groups, and carbamoylamino ($C_1$–$C_4$ alkoxy) groups;

$R_4$ is chosen from hydrogen, halogens, and $C_1$–$C_4$ alkyl groups.

11. The composition according to claim 10, wherein when $R_3$ or $R_4$ is a halogen, said halogen is chosen from chlorine, bromine, iodine and fluorine.

12. The composition according to claim 10, wherein said para-phenylenediamines of formula (I) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methyl-aniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxy propyl)-para-phenylene-diamine, N-(4'-aminophenyl)-para-phenylenediamine, N-phenyl-paraphenylenediamine, 2-β-hydroxyethyl-oxypara-phenylenediamine, 2-β-acetylaminoethyloxy-para-phenylenediamine, N-(β-methoxyethyl)-para-phenylenediamine, and their acid addition salts.

13. The composition according to claim 9, wherein said double bases are chosen from compounds of the following formula (II), and their acid addition salts:

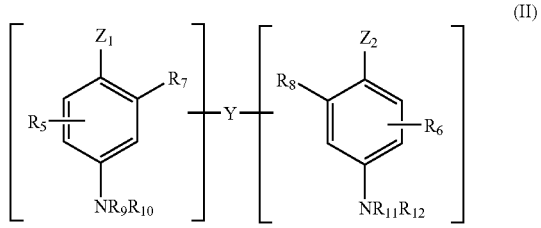

in which:

Z₁ and Z₂, which may be identical or different, are each chosen from hydroxyl groups and an —NH₂ group, each of which may be optionally substituted with a group chosen from $C_1$–$C_4$ alkyl groups and a linking arm Y;

the linking arm Y is chosen from linear and branched alkylene groups comprising from 1 to 14 carbon atoms, which optionally may be interrupted by, or which optionally may end with at least one nitrogen-containing group and/or at least one heteroatom, and which optionally may be substituted with at least one group chosen from hydroxyl groups and $C_1$–$C_6$-alkoxy groups;

$R_5$ and $R_6$, which may be identical or different, are each chosen from hydrogen, halogens, $C_1$–$C_4$ alkyl groups, monohydroxy ($C_1$–$C_4$ alkyl) groups, polyhydroxy-($C_2$–$C_4$ alkyl) groups, ($C_1$–$C_4$ alkyl) groups, and a linking arm Y;

$R_7$, $R_8$, $R_9$, $R_{10}$, $R_{11}$, and $R_{12}$, which may be identical or different, are each chosen from hydrogen, a linking arm Y, and ($C_1$–$C_4$ alkyl) groups; wherein the compounds of formula (II) contain only one linking arm Y per molecule.

14. The composition according to claim 13, wherein said at least one heteroatom of the linking arm Y is chosen from oxygen, sulfur, and nitrogen.

15. The composition according to claim 13, wherein said double bases of formula (II) are chosen from N,N'-bis(β-hydroxyethyl)-N,N'-bis(4'-amino-phenyl)-1,3-diaminopropanol, N,N'-bis(β-hydroxyethyl)-N,N'-bis (4'-aminophenyl) ethylenediamine, N,N'-bis(4-aminophenyl) tetramethylenediamine, N,N'-bis(β-hydroxyethyl)-N,N'-bis-(4-aminophenyl)tetramethylenediamine, N,N'-bis(4-methylamino-phenyl)-tetramethylenediamine, N,N'-bis(ethyl)-N,N'-bis( 4'-amino-3'-methylphenyl) ethylenediamine, 1,8-bis(2,5-diaminophenoxy)-3,5-dioxaoctane, and the acid addition salts of said double bases.

16. The composition according to claim 9, wherein said para-aminophenols are chosen from the compounds of formula (III), and their acid addition salts:

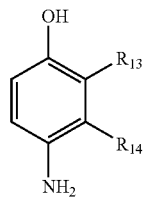

in which:

$R_{13}$ is chosen from hydrogen, halogens, $C_1$–$C_4$ alkyl groups, monohydroxy($C_1$–$C_4$ alkyl) groups, ($C_1$–$C_4$) alkoxy($C_1$–$C_4$)-alkyl groups, amino($C_1$–$C_4$ alkyl) groups, and hydroxy($C_1$–$C_4$)alkylamino-($C_1$–$C_4$ alkyl) groups;

$R_{14}$ is chosen from hydrogen, halogens, $C_1$–$C_4$ alkyl groups, monohydroxy($C_1$–$C_4$ alkyl) groups, polyhydroxy ($C_2$–$C_4$ alkyl) groups, amino($C_1$–$C_4$ alkyl) groups), cyano($C_1$–$C_4$ alkyl) groups, and ($C_1$–$C_4$) alkoxy($C_1$–$C_4$)alkyl groups;

wherein at least one of $R_{13}$ or $R_{14}$ is a hydrogen atom.

17. The composition according to claim 16, wherein said para-aminophenols of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxy methylphenol, 4-amino-2-amino-methylphenol, 4-amino-2-(β-hydroxy-ethylaminomethyl)phenol, 4-amino-2-fluoro-phenol, and their acid addition salts.

18. The composition according to claim 9, wherein said ortho-aminophenols are chosen from 2-aminophenol, 2-amino-5-methylphenol, 2-amino-6-methylphenol, 5-acetamido-2-aminophenol, and their acid addition salts.

19. The composition according to claim 9, wherein said heterocyclic oxidation bases are chosen from pyridine derivatives, pyrimidine derivatives, pyrazole derivatives, pyrazolopyrimidine derivatives, and their acid addition salts.

20. The composition according to claim 1, wherein said at least one colorant is present in a concentration ranging from about 0.0005% to about 12% by weight of the total weight of said composition.

21. The composition according to claim 1, wherein said at least one colorant is present in a concentration ranging from about 0.005% to about 6% by weight of the total weight of said composition.

22. The composition according to claim 1, wherein said at least one coupler is present in a concentration ranging from about 0.0001% to about 8% by weight of the total weight of said composition.

23. The composition according to claim 1, wherein said at least one coupler is present in a concentration ranging from about 0.005% to 5% by weight of the total weight of said composition.

24. The composition according to claim 1, further comprising at least one additional coupler different from 2-amino-4-N-(β-hydroxyethyl)aminoanisole and/or at least one direct dye.

25. The composition according to claim 1, wherein said acid addition salts of said at least one oxidation base are chosen from hydrochlorides, hydrobromides, sulphates, tartrates, lactates, and acetates.

26. The composition according to claim 1, wherein said acid addition salts of said at least one coupler are chosen from hydrochlorides, hydrobromides, sulphates, tartrates, lactates, and acetates.

27. The composition according to claim 1, further comprising at least one carrier appropriate for dyeing keratinous fibers.

28. The composition according to claim 26, wherein said at least one carrier is chosen from water and organic solvents.

29. The composition according to claim 1, wherein said composition has a pH ranging from about 4 to about 11.

30. A method of dyeing keratinous fibers, comprising the step of applying at least one dyeing composition to said keratinous fibers for a sufficient time to achieve a desired coloration, wherein said at least one dyeing composition comprises:
 (a) at least one colorant chosen from oxidation bases and their acid addition salts;
 (b) at least one coupler chosen from 2-amino-4-N-(β-hydroxyethyl)aminoanisole and acid addition salts of said coupler; and
 (c) at least one enzyme of the laccase type.

31. A method for dyeing keratinous fibers comprising the steps of:
 (a) storing a first composition;
 (b) storing a second composition separately from said first composition;
 (c) mixing said first composition with said second composition to form a mixture; and
 (d) applying said mixture to said keratinous fibers for a sufficient time to achieve a desired coloration;
 wherein said first composition comprises at least one colorant chosen from oxidation bases and their acid addition salts and at least one coupler chosen from 2-amino-4-N-(β-hydroxyethyl)aminoanisole and acid addition salts of said coupler in a medium appropriate for dyeing keratinous fibers, and
 wherein said second composition (b) comprises at least one enzyme of the laccase type, in a medium suitable for dyeing keratinous fibers.

32. A multi-compartment device or a dyeing kit, comprising:
 a first compartment containing a first composition comprising at least one colorant chosen from oxidation bases and their acid addition salts and at least one coupler chosen from 2-amino-4-N-(β-hydroxyethyl)aminoanisole and acid addition salts of said coupler, in a medium appropriate for dyeing keratinous fibers; and
 a second compartment containing a second composition comprising at least one enzyme of the laccase type, in a medium suitable for dyeing keratinous fibers.

33. The composition according to claim 1, wherein said at least one enzyme of the laccase type is chosen from laccases of fungal origin.

34. The composition according to claim 33, wherein said laccases of fungal origin are obtained by biotechnology.

35. The composition according to claim 1, wherein said at least one enzyme of the laccase type is chosen from laccases of plant origin, laccases of animal origin, laccases of fungal origin and laccases of bacterial origin.

36. The composition according to claim 1, wherein said at least one enzyme of the laccase type is chosen from laccases obtained by biotechnology.

* * * * *